United States Patent [19]

Tanner, II

[11] 3,967,729
[45] July 6, 1976

[54] FULLY SEALED PACKAGE FOR STERILE CONTENTS

[75] Inventor: John Clinton Tanner, II, Hinsdale, Ill.

[73] Assignee: Johnson & Johnson, New Brunswick, N.J.

[22] Filed: Sept. 29, 1975

[21] Appl. No.: 617,903

[52] U.S. Cl. .............................. 206/440; 206/813; 229/62; 229/80
[51] Int. Cl.² .......................................... A61B 19/02
[58] Field of Search ........... 206/438, 439, 440, 813; 229/62, 80, 48 T

[56] References Cited
UNITED STATES PATENTS

| | | | |
|---|---|---|---|
| 3,070,225 | 12/1962 | Schwartz | 206/438 |
| 3,478,868 | 11/1969 | Nerenberg et al. | 206/439 |
| 3,873,404 | 3/1975 | West | 206/813 |

FOREIGN PATENTS OR APPLICATIONS

| | | | |
|---|---|---|---|
| 697,750 | 11/1964 | Canada | 206/440 |

Primary Examiner—George E. Lowrance
Assistant Examiner—Bruce H. Bernstein
Attorney, Agent, or Firm—J. Lipow

[57] ABSTRACT

A package is provided especially for containing sterile articles which can be readily opened and which provides for the controlled removal of the contents. The package is sealed in a manner which precludes the formation of channels leading to the interior of the package and compromises sterility. Specifically, the end seal of the package is provided by providing a thermoplastic adhesive which acts as a caulk to seal such potential channels, the thermoplastic adhesive being disposed in a manner whereby it is assured that said adhesive does not contact adhesively incompatible areas.

6 Claims, 10 Drawing Figures

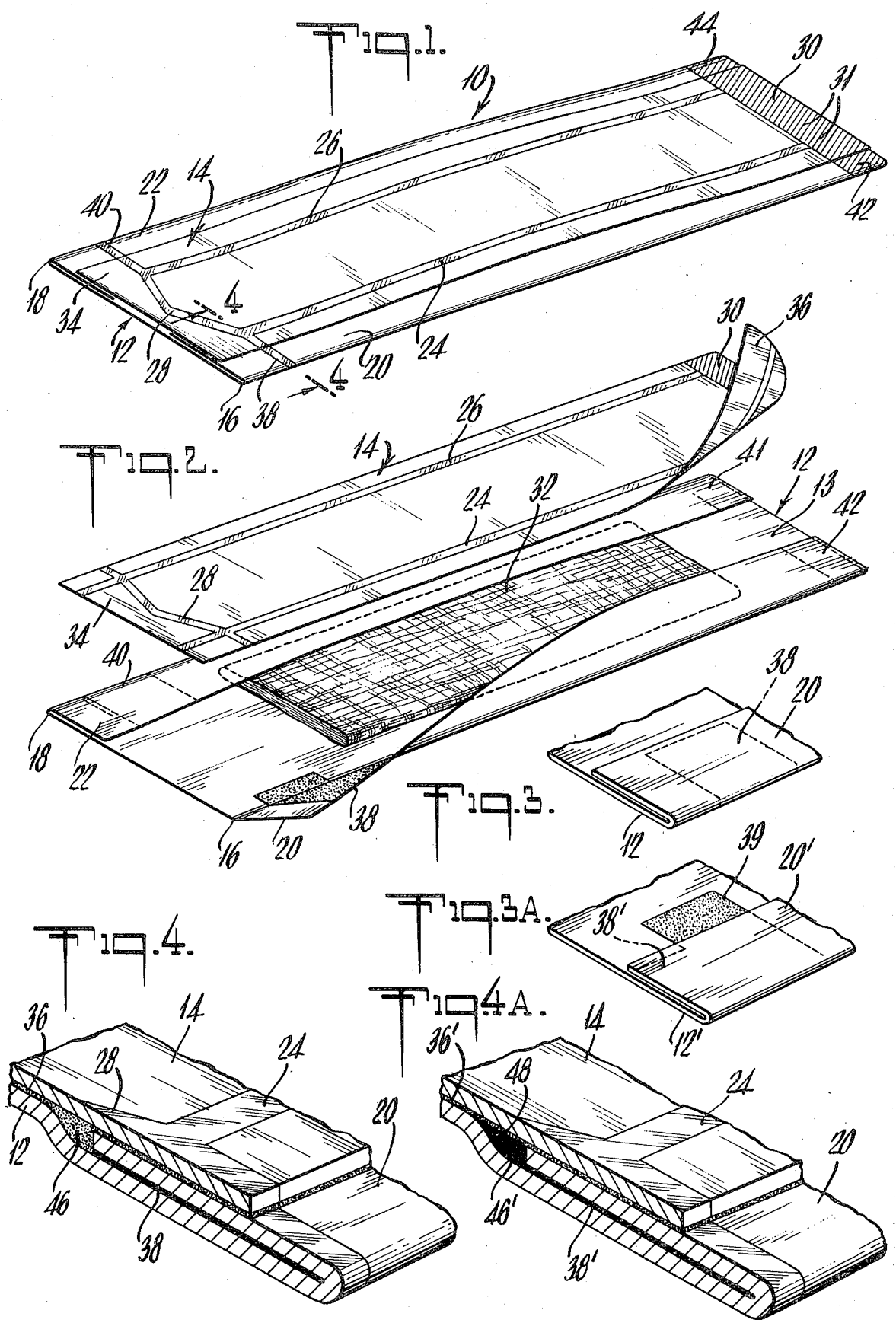

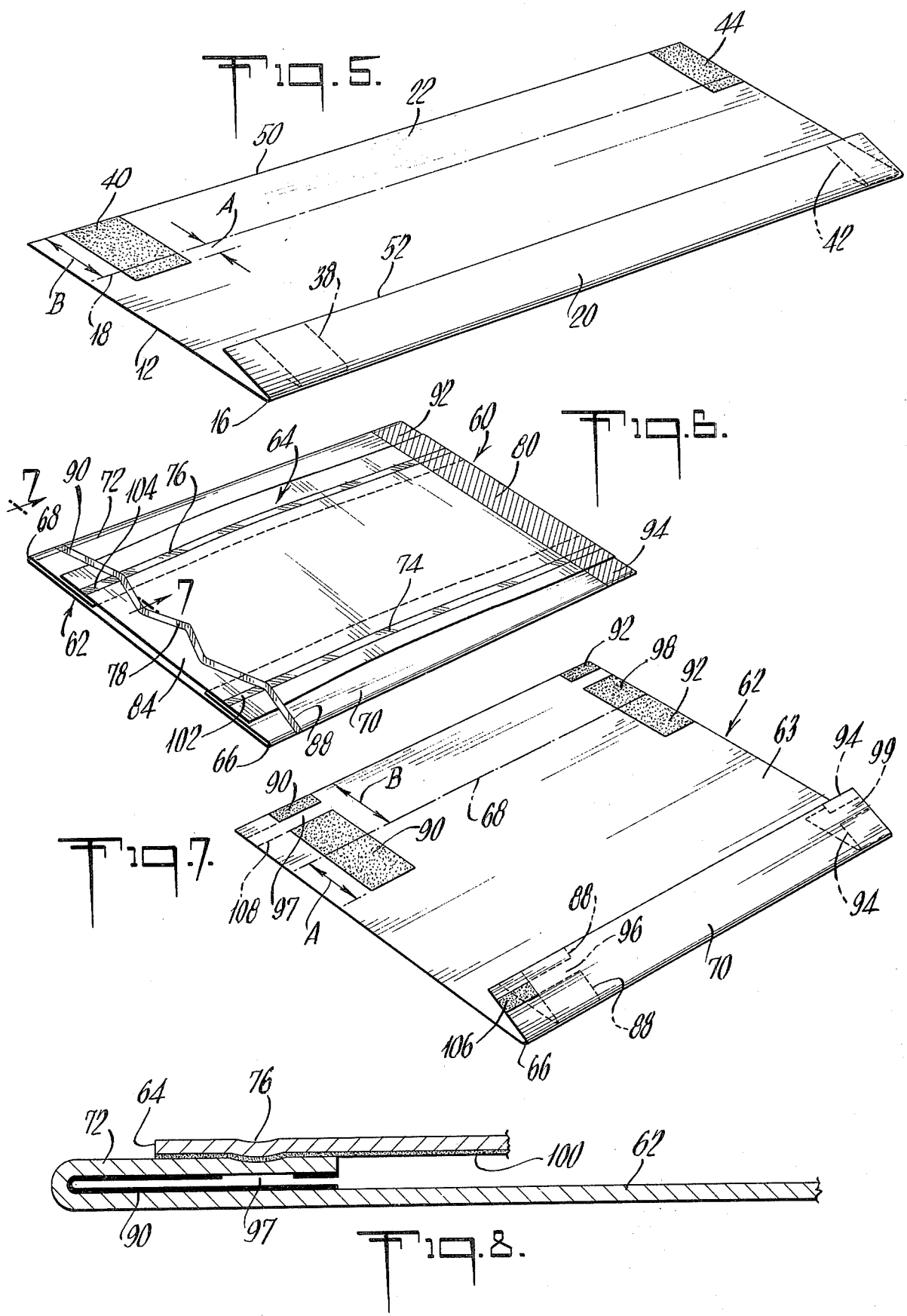

FULLY SEALED PACKAGE FOR STERILE CONTENTS

BACKGROUND OF THE INVENTION

This invention relates to improved packages and more particularly, to packages which can be sterilized by conventional means after sealing, which are capable of maintaining the sterility of the contents, which can be readily opened and which provide for the controlled removal of the contents by a sterile technique.

Surgical articles and the like have been packaged and then sterilized in order to reduce the hazard of cross-infection in hospitals. Many of the packages previously employed have, however, been found to have serious disadvantages. Some of these, for example, have been difficult to open, requiring tearing or cutting and, hence, exposing the article, when withdrawn, to contamination by the non-sterile, exterior, torn or cut edges of the package. Other prior packages have suffered from the disadvantage of not permitting positive control of the sterile contents while opening the package to prevent the contents from dropping out and being contaminated. Another disadvantage of some prior packages is that they have been found to have unsealed channels through the seal lines closing the package at points where more than two sheets of packaging material are joined. Packages of this type tend to breathe, particularly when stored under conditions where there is a wide variation in temperature or atmospheric pressure. This is highly disadvantageous since it makes possible the introduction of airborne bacteria which may contaminate the contents of the package and cause the loss of sterility.

U.S. Pat. No. 3,070,225, issued on Dec. 25, 1962 to M. A. Schwartz and U.S. Pat. No. 3,324,705, issued on Feb. 15, 1966, also to M. A. Schwartz, disclose packaging for sterile articles and, in particular, disclose that the channel problem, referred to above, may be solved by providing a thermoplastic "calking" adhesive to flow into and block such potential channels. The concept disclosed is to provide a package comprising a top and bottom sheet. The bottom sheet has a peripheral portion or side edge of each of its longitudinal sides folded inwardly to overlie the bottom sheet and form longitudinally extending side flanges. The article packaged may then be partially held under the flanges in a controlled and positive manner. These side flanges are tacked down by applied, spaced areas of adhesive. A top sheet is then laid over the bottom sheet with the article and the side flanges therebetween. The top sheet is sealed to the bottom sheet by longutidinal side seals in the area where the top sheet overlies the side flanges and by transverse end seals spanning the two side flanges. The problem of channeling toward which the Schwartz patents are directed occurs at the end seals where the seal passes first through at least three thickness of packaging material (corresponding to the bottom sheet, the flange at one side and the top sheet), then two thickness (corresponding to the top sheet and the bottom sheet) and then again three thickness (corresponding to the bottom sheet, the flange at the other side, and the top sheet). It is at the point where the seal crosses from three to two thickness of packaging material, that the channeling problem exists. The solution suggested in the aforementioned Schwartz patents is to provide, for the spaced adhesive areas used on the bottom sheet for tacking down the flanges, a thermoplastic adhesive which is applied to the bottom sheet so as to extend beyond the area of contact between the flange and the bottom sheet. In this manner, when heat and pressure are applied to produce the end seal, at the same time the thermoplastic adhesive will be activated and become flowable, thus acting as a calk to block the potential channels.

This solution has been highly satisfactory and is particularly effective when both the top sheet and the bottom sheet are provided with the same, or otherwise adhesively compatible, adhesives. By the term "adhesively compatible adhesives" it is meant two adhesives which, upon activation, will seal together at their interface. Unfortunately, it is not always possible or desirable to provide the top and bottom sheets with adhesively compatible adhesives. In the circumstance where the adhesive applied to the top sheet for side and end sealing is adhesively incompatible with the adhesive used on the bottom sheet to tack down the flanges, the solution offered by the aforementioned Schwartz patents is not only inappropriate, but actually aggravates the problem. In this case, the calking adhesive does flow, upon end sealing. Instead of creating a seal, however, a relatively long interface of noncompatible top and bottom sheet adhesive is created at portions of the end seal between and adjacent to each flange. Accordingly, because of the incompatibility of the adhesives, this long interface is, in effect, a channel into the interior of the package, rendering the same entirely unsuitable for sterile articles.

It is apparent, therefore, that the need exists for a package for sterile articles which does not suffer from these drawbacks.

SUMMARY OF THE INVENTION

In accordance with this invention, a package is provided which utilizes the general construction described in the aforementioned patents to Schwartz, but does not suffer from the drawbacks associated therewith when it is desirable to employ adhesively incompatible adhesives.

Specifically, the invention is directed to a package for containing a sterile article of the type comprising a bottom sheet having an inner surface and folded side edges providing longitudinally extending side flanges. A top sheet having an inner surface is provided overlying the inner surface and flanges of the bottom sheet. The two sheets are held together and form a chamber therebetween by means of a peripheral seal comprising two side seals bonding the sides of the top sheet to the flanges of the bottom sheet and two end seals bonding the ends of the top sheet to the ends of the flanges and to the ends of the inner surface of the bottom sheet between the flanges.

As in the Schwartz patents, a first adhesive is disposed on the inner surface of the bottom sheet in the areas which contact the flanges under the end seals to provide means for sealing the ends of the package under the flanges. The top sheet is provided with an overall coating of a thermoplastic adhesive which is adhesively incompatible with the first adhesive. The necessity for adhesive incompatibility between the top and bottom sheet adhesives arises from several considerations. Firstly, it is desirable that the top sheet be overall coated as this eliminates the need for perfect registration when sealing the top sheet to the bottom sheet. In connection with this, it is then necessary to accurately apply the first adhesive to limited areas on the bottom sheet with means such as printing being best adapted for this purpose. Thus, because one adhesive is to be overall coated while the other is to be printed, it is difficult to find adhesively compatible materials which lend themselves to both methods of application.

The side seals of the package are effected by applying heat and pressure along the sides of the package to activate the thermoplastic adhesive and hence, bond the sides of the top sheet to the flanges. The end seals are effected by again applying heat and pressure along the ends of the package, activating both the first adhesive under the flanges and the thermoplastic adhesive on the top sheet.

As described above, there is a tendency to form a channel into the package at a point in the end seal adjacent the flange edge. In accordance with the method of the aforementioned Schwartz patent, the solution to this problem is to extend the area of first adhesive disposed on the inner surface of the bottom sheet to a point inward of the package and beyond the edge of the flange. When activated, this adhesive acts as a calk to seal the channel. However, when the adhesive on the top sheet is adhesively incompatible with the first adhesive, a long non-sealed interface results and aggravates the problem. Accordingly, in contrast to the prior method and in accordance with the method taught herein, the disposition of the first adhesive is limited to only the areas of contact between the inner surface of the flange and the inner surface of the bottom sheet which lie under the end seals. The portion of the inner surface of the bottom sheet between flanges and under the end seal are free of the first adhesive. Said in other words, in the area of the end seal, at no point does the thermoplastic adhesive on the top sheet contact the first adhesive on the bottom sheet to form a non-adhering interface. Instead, upon applying heat and pressure to form the end seal, both the first adhesive and the thermoplastic adhesive are activated and it is the thermoplastic adhesive, overall coated on the top sheet which fills the potential channels existing at the edge of the flanges.

A better understanding of the invention and the advantages which accrue therefrom will be had be referring to the appended drawings taken in connection with the following detailed description.

BRIEF DESCRIPTION OF THE DRAWINGS

FIG. 1 is a perspective view of a package embodying the instant invention;

FIG. 2 is a perspective, exploded view of the package of FIG. 1 with the one edge of the top sheet and one edge of a flange turned up to expose the inner surfaces thereof;

FIG. 3 is an enlarged, perspective view of the portion of the bottom sheet illustrated in FIG. 2 at one side of the end seal of the package;

FIG. 3A is an enlarged, perspective view of a portion of a prior art package corresponding to that of FIG. 3;

FIG. 4 is an enlarged, perspective, cross-sectional view of a portion of the end seal of the package illustrated in FIG. 1 and taken through line 4—4;

FIG. 4A is an enlarged, cross-sectional view of a part of the end seal of a prior art package corresponding to that of FIG. 4;

FIG. 5 is a perspective view of a partially folded bottom sheet employed in the package of FIG. 1;

FIG. 6 is a perspective view of a second package embodying the instant invention;

FIG. 7 is a perspective view of a partially folded bottom sheet employed in the package of FIG. 6; and FIG. 8 is an enlarged, cross-sectional view of a portion of the end seal area of the package illustrated in FIG. 6 prior to effecting the end seal and subsequent to effecting the side seal.

DETAILED DESCRIPTION OF THE INVENTION

Referring to FIGS. 1 and 2 of the drawings, the package 10 is formed from a bottom sheet 12 having an inner surface 13 and a top sheet 14. The side edges of the bottom sheet 12 are folded, along fold lines 16 and 18 to form longutidinally extending side flanges 20 and 22. The top sheet overlies both the bottom sheet and at least a portion of the flanges and is bonded thereto by a peripheral seal comprising side seals 24 and 26 and end seals 28 and 30. A sterile article, exemplified by the surgical sponge 32, may be placed within the chamber formed between the top and bottom sheets and held there in a controlled manner by the flanges 20 and 22. As shown in the drawings, end seal 28 is designed to be the mouth of the package and, accordingly, this end seal 28 is disposed at a point inward of the extreme end of the package so as the provide a tab portion 34 which may be gripped to peel back the top sheet 14 when opening the package 10. To this end, the end seal 18 is preferably in a v-shaped to reduce the forces required when peeling the package open from this end.

It is contemplated that the side seals 24 and 26 will be accomplished by applying heat and pressure with a heated sealing bar pressed against the externally facing surface of the top sheet to seal the sides of the top sheet to the flanges 20 and 22. Likewise, end seals 28 and 30 will similarly be affected by appropriately shaped heated sealing bars. It is therefore advantageous to apply a coating of thermoplastic adhesive 36 to the inner surface of the top sheet and further, rather than merely applying this adhesive to those areas lying directly under the seals, it is perferable to overall coat the inner surface of the top sheet. In this manner, the need for careful registration of the top and bottom sheet is avoided and even a gross misregistration will provide effective sealing. A wide variety of thermoplastic materials may be employed as this coating using such methods as extrusion coating, or the lamination of thermoplastic films onto the inner surface of the top sheet. Examples of suitable thermoplastic adhesives are both high and low density polyethylene, polypropylene, and the like.

By bonding the top sheet to the flanges, the sides of the package are effectively sealed against the intrusion of non-sterile matter.

In the case of the end seals, however, it is also necessary to seal the areas of contact, 38, 40, 42 and 44, underlying the end seals and between the inner surface of the bottom sheet and the inner surface of the flanges. Accordingly, an adhesive is disposed in these areas of contact, the adhesive being activated by the application of heat and pressure when the end seal is affected. Because this adhesive must be applied to discrete areas of contact, it is necessary to use a material which is capable of being accurately placed in a desired pattern by such methods as pattern printing. Generally, such printing methods involve passing the web on which the pattern is to be printed through print rollers which are embossed or engraved with the required pattern and which have passed through a reservoir of an emulsion of adhesive. Accordingly, the adhesive material chosen should be one capable of forming such an emulsion and preferably an aqueous emulsion, with polyvinyl acetate being the adhesive of choice. Unfortunately, such adhesives are adhesively incompatible with the thermoplastic adhesives preferred as an overall coating for the top sheet and this adhesive incompatibility gives rise to the problem of channeling, the solution to which this invention is directed.

Referring now to FIGS. 3, 3A, 4 and 4A, illustrated in FIG. 3 is an enlarged, perspective view of the portion of flange 20 and the bottom sheet 12 underlying end seal 28. It will be understood, this portion is typical of the remaining three areas under the end seals. FIG. 3A illustrates a portion of the prior art package, as disclosed in the aforementioned M. A. Schwartz patents, with primed numerals referring to parts corresponding to parts of the package of this invention.

Similarly, FIG. 4 illustrates, in perspective cross-section, a view of this same portion of the package of FIG. 1, and FIG. 4A illustrates a corresponding portion of the prior art package, again with primed numerals referring to corresponding parts.

As can be best seen in FIGS. 4 and 4A, as the end seal 28 passes from the edge of the package toward the center, the number of thickness of material being sealed together changes from three (corresponding to the top sheet 14, the flange 20 and the bottom sheet 12) to two (corresponding to the top sheet 14 and the bottom sheet 12). Accordingly, there is the tendency to form a channel into the package at the area 46 where the change in the number of thickness occurs.

Referring to FIG. 3A, the prior art method of solving this problem is to provide an adhesive coated area 38', employing a thermoplastic adhesive. This adhesive area is provided with an extended portion 39, extending beyond the area of contact between the flange 20' and the bottom sheet 12'. Thus, when heat and pressure are applied, the adhesive of this extended portion 39 will flow and act as a calk to fill the area 46', as is illustrated in FIG. 4A. Such a prior art method is effective, however, only when the adhesive coating 36' and 38' are adhesively compatible. As is illustrated in FIG. 4A, by employing the method of Schwartz, a relatively long transverse interface 48 is formed. When, for the reasons discussed above, it becomes necessary to employ adhesively incompatible adhesives for adhesives 36' and 46', this interface remains unsealed and results in a substantial channel into the interior of the package, thus severly compromising the sterility of the contents and making the solution disclosed by Schwartz wholly inappropriate.

In accordance with the instant invention, as illustrated in FIG. 3, the adhesive 38 is limited to the area of contact between the bottom sheet 12 and the flange 20. The area under the end seal 28 beyond flange 20 and between this flange and flange 22 is maintained free of such adhesive. To solve the aforementioned channeling problem, the adhesive 36, applied to the top sheet, is selected as a thermoplastic adhesive and, as can be best viewed in FIG. 4, it is this adhesive which flows into the area 46, sealing the potential channel. Because the adhesive 36 never makes substantial contact with adhesive 38, no non-adhering interface is formed and the fact that the two adhesives are adhesively in no way compromises the sterility of the contents.

Illustrated in FIG. 5 is a partially folded perspective view of the bottom sheet 12, shown with one side edge folded along fold line 16 to form flange 20. The other side edge has not yet been folded along line 18. Printed onto the bottom sheet 12 are the four adhesive areas 38, 40, 42, and 44. As is described above, it is important that the printing be such that upon folding the side edges to form flanges 20 and 22, each of the adhesive areas are limited to the area of contact between the flanges and the bottom sheet. To assure this, the printed areas are limited in the transverse direction to an inward distance A beyond the fold lines 16 and 18, respectively, which is less than the width B of the flanges. To assure that the flanges are fully bonded to the bottom sheet, the adhesive is applied to extend to the very edges 50 and 52 of the bottom sheet.

In manufacturing the package 10 illustrated in FIG. 1, it is contemplated that after superimposing top sheet 14 upon bottom sheet 12, end seal 30 and side seals 24 and 26 will be effected, forming an envelope with an open mouth for filling. In this connection, end seal 30 may be strengthened by applying crimps 31 either during or after the heat sealing operation. Upon filling, end seal 28 will be effected. As described above, and as is illustrated in FIG. 2, it is desirable that a portion of the contents 32 of the package be sandwiched between the flanges 20 and 22 and the bottom sheet so that when the package is peeled open, the contents will be held in place in a positive controlled manner. In order to do this, it is necessary that, upon effecting the side seals prior to filling, care is taken to avoid activating the adhesive in areas 38 and 40 in that should these areas be sealed, it will be difficult, if not impossible, to fill the package with the contents held under the flanges. Accordingly, in the embodiment shown in FIG. 1, the side seals must terminate at a point short of the adhesively applied areas 38 and 40 and the package sealed completely closed only after effecting end seal 28, e.g., by having end seal 28 be wide enough to slightly overlap the ends of side seals 24 and 26.

The need to prevent premature sealing of the adhesive areas 38 and 40 necessitates an interrupted application of heat sealing bars when effecting side sealing on a mass production basis. In another aspect of this invention, the printed pattern of adhesive areas 38, 40, 42, and 44 is varied to allow instead of continuous side sealing. Referring now to FIGS. 6–8, illustrated in FIG. 6 is a second embodiment of this invention, generally designated as package 60. As in the prior embodiment, package 60 is formed from a bottom sheet 62 having an inner surface 63 and a top sheet 64.

The side edges of the bottom sheet 62 are folded along fold lines 66 and 68 to form longitudinally extending side flanges 70 and 72. The top sheet overlies both the bottom sheet and at least a portion of the flanges and is bonded thereto by a peripheral seal comprising side seals 74 and 76 and end seals 78 and 80. End seal 78 is designed to be the mouth of the package and accordingly, this seal is disposed at a point inward of the extreme end of the package so as to provide a tab portion 84 which may be gripped to peel back the top sheet 64 when opening the package 60. As shown in this embodiment, the end seal 78 is provided in a pattern of multiple peak to reduce the forces required when opening the package. While this pattern is interchangeable with the v-shaped described in connection with FIG. 1, the multiple peak pattern eliminates the need for perfect registration of the end sealing bar when effecting the seal.

As in the prior embodiment, top sheet 64 is provided on its inner surface with an overall coating of a thermoplastic adhesive to effect the side and end seals by the application of heat and pressure. Again, an adhesive, incompatible with the thermoplastic adhesive on the top sheet, is applied in the areas of contact 88, 90, 92 and 94 underlying the end seals and between the flanges 70 and 72 and the bottom sheet 62. In accordance with this invention, these applications of adhesive are limited to the area of contact. The portion of the bottom sheet 72 lying under the end seals and between the flanges are free of this adhesive.

Unlike the side seals of FIG. 1, side seals 74 and 76 are effected by passing the full length of the package under a heated sealing bar so that a plurality of packages can be side sealed in a continuous manner. In accordance with this aspect of the invention, to avoid premature sealing of the flanges, the pattern of adhesive applied to the bottom sheet is varied from that of the prior embodiment, as is best illustrated in FIG. 7.

Referring now to FIG. 7, illustrated therein is a partially folded, perspective view of the bottom sheet 62, shown with one side edge folded along fold line 66 to form flange 70. The other side edge has not yet been folded along line 68. Printed onto the bottom sheet 62 are the four adhesive areas 88, 90, 92 and 94. Again, in accordance with this invention, the adhesive is limited to the area of contact between the flanges and the bottom sheet and so the adhesive areas are printed in a pattern such that the trasnverse inward distance A beyond the fold lines 66 and 68 is less than the width B of the flanges.

In accordance with this aspect of the invention, the printed adhesive areas are provided with gaps 96, 97, 98 and 99 corresponding to the area through which the continuous side seals 74 and 76 will pass. The effect of the gaps is best understood by referring to FIG. 8 which is a cross-sectional view of a portion of package 60 of FIG. 6 taken through line 7—7 at a time prior to effecting the end seal 78 and subsequent to effecting the side seal 76. It can be seen from this figure, that by passing the package continuously under a heat sealing bar, side seal 76 has been effected and the thermoplastic adhesive 100 coated to the top sheet 64 has been bonded to the flange 72. By virtue of the gap 97 in the applied adhesive area 90, the heat and pressure exerted by the bar can be controlled to avoid activating the adhesive area 90 when side seal 76 is effected. Said in other words, the absence of adhesive on the inner surface of flange 72, under side seal 76, insures that adhesive area 90 at this point is sufficiently remote from the application of heat and pressure applied in effecting side seal 76 so that such heat and pressure can be controlled to avoid activating any of the adhesive area 90 under the seal. Thus, the flange 72 will remain unbonded to the inner surface of bottom sheet 62 and the package may easily be filled to hold the contents in a controlled manner.

Referring once again to FIG. 6, package 60 is designed to be opened at the end adjacent to seal 78 and accordingly, this seal is disposed at a point inward of the extreme end of the package to provide a tab portion 84 which may be gripped to peel back the top sheet 64. To facilitate gripping the tab, it is preferred that the terminal portions 102 and 104 of the side seals 74 and 76, respectively, remain unbonded to the flanges 70 and 72. A simple means for affecting this is illustrated in FIG. 7. Printed onto the exterior surface of the bottom sheet 62 are areas 106 and 108. These areas are printed with a material (e.g., the adhesive 90) adhesively incompatible with the thermoplastic adhesive coating 100 on the top sheet and are placed in those areas of contact between the flanges and the superimposed top sheet which corresponds to the terminal portions 102 and 104 of the side seals 74 and 76. Accordingly, even though the sealing bar will continuously pass over these terminal portions and activate the thermoplastic adhesive 100 thereunder, because this portion of the adhesive coating 100 is opposed by an adhesively incompatible area, the top sheet will not bond to the flange in this area and the tab 84 will remain free for gripping. Many variations in the above-described embodiments are possible while still remaining within the scope and spirit of this invention. For example, while the above embodiments have been described in terms of packages 10 and 60, these being opened by peeling the respective top sheets back from the bottom sheets in a direction parallel to the side seals, it is equally possible to peel the top sheet back in a direction transverse to these side seals. In this case, the package would be opened by gripping a side edge of the top sheet and pulling it back to break the adjacent side seal and the two end seals to provide access to the contents. The method of opening the package notwithstanding, the teachings herein relating to the problem of channeling, when using adhesively incompatible materials, still apply.

The top and bottom sheets may be composed of any suitable, flexible packaging material. It is preferred, however, that at least one of these elements be composed of a flexible packaging material which permits sterilization of the contents of the package subsequent to sealing. Paper is most suitable for this purpose, since it permits sterilization by steam or sterilizing gases according to conventional procedures. Especially suitable for this purpose is a sterilizable bacterial barrier paper having a 35–40 lb. per ream basis weight, although higher weights, e.g. 60 lbs. per ream, is also suitable.

What is claimed is:

1. In a package for containing a sterile article and comprising:

a bottom sheet having an inner surface and folded side edges folded along longitudinally extending fold lines providing longitudinally extending side flanges;

a top sheet having an inner surface and overlying the inner surface and flanges of said bottom sheet; and a peripheral seal comprising side seals bonding the sides of the top sheet to the flanges of said bottom sheet and end seals bonding the ends of said top sheet to the ends of the flanges and the ends of the inner surface of the bottom sheet therebetween;

the improvement which comprises:

a first adhesive disposed on the inner surface of said bottom sheet in the areas which contact said folded side edges and are under said end seals, said first adhesive being limited within said areas of contact with the area between said flanges and under said end seal being free of said first adhesive;

a thermoplastic adhesive, adhesively incompatible with said first adhesive, overall coating the inner surface of said top sheet;

said side seals of said package being affected by heat and pressure applied along the sides of the package and activating said thermoplastic adhesive and said end seals affected by heat and pressure applied along the ends activating both said first adhesive and said thermoplastic adhesive with said thermoplastic adhesive filling any channels existing along said flanges between said bottom sheet and said cover sheet.

2. The package of claim 1 wherein said disposition of said first adhesive is limited in a transverse direction to an inward distance beyond said fold lines which distance is less than the width of said side flanges.

3. The package of claim 1 wherein said side seals terminate at a point short of the disposed first adhesive at at least one end of said package whereby said package may be filled prior to effecting the end seal at said at least one end of said package.

4. The package of claim 1 wherein said side seals are applied continuously and gaps provided in said disposed first adhesive at at least one end of said package, said gaps underlying said continuously applied side seal whereby said package may be filled prior to affecting the end seal at said at least one end of said package.

5. The package of claim 1 wherein at least one end seal is disposed inwardly of the end of said package to provide a tab for peelably opening said package.

6. The package of claim 5 wherein said side seals are continuous and means are provided for precluding sealing of said top sheet to said flanges in the area of said tab, said means comprising an adhesively incompatible material disposed on said flanges in the area of said tab underlying said side seals.

* * * * *

UNITED STATES PATENT AND TRADEMARK OFFICE
CERTIFICATE OF CORRECTION

PATENT NO. : 3,967,729
DATED : July 6, 1976
INVENTOR(S) : Tanner, John Clinton III It is certified that error appears in the above-identified patent and that said Letters Patent are hereby corrected as shown below:

In Column 3, line 62, "enlarged, cross-sectional" should read -- enlarged, perspective, cross-sectional --.

In Column 4, line 24, "so as the provide" should read -- so as to provide --.

In Column 4, line 26, "the end seal 18" should read -- the end seal 28 --.

In Column 5, line 53, "the adhesive 38" should read -- the adhesive area 38 --.

In Column 5, line 65, " adhesively in no way" should read -- adhesively incompatible in no way --.

In Column 6, line 45, "instead of continuance" should read -- instead for continuance --.

Signed and Sealed this

Fifteenth Day of February 1977

[SEAL]

Attest:

RUTH C. MASON
Attesting Officer

C. MARSHALL DANN
Commissioner of Patents and Trademarks